United States Patent
Batchelor et al.

(10) Patent No.: US 10,327,835 B2
(45) Date of Patent: Jun. 25, 2019

(54) HEAT PIPE COOLING ARRANGEMENT FOR ELECTROSURGICAL DEVICES

(71) Applicant: GYRUS ACMI, INC., Southborough, MA (US)

(72) Inventors: Kester J. Batchelor, Mound, MN (US); John R. Mensch, Plymouth, MN (US)

(73) Assignee: GYRUS ACMI, INC., Southborough, MA (US)

( * ) Notice: Subject to any disclaimer, the term of this patent is extended or adjusted under 35 U.S.C. 154(b) by 409 days.

(21) Appl. No.: 14/672,525

(22) Filed: Mar. 30, 2015

(65) Prior Publication Data
US 2015/0282873 A1    Oct. 8, 2015

Related U.S. Application Data

(60) Provisional application No. 61/973,955, filed on Apr. 2, 2014.

(51) Int. Cl.
*A61B 18/00* (2006.01)
*A61B 18/14* (2006.01)

(52) U.S. Cl.
CPC ...... *A61B 18/1445* (2013.01); *A61B 18/1442* (2013.01); *A61B 2018/00005* (2013.01); *A61B 2018/00023* (2013.01); *A61B 2018/00101* (2013.01); *A61B 2018/00607* (2013.01); *A61B 2018/1452* (2013.01); *A61B 2018/1455* (2013.01); *A61B 2218/007* (2013.01); *A61B 2218/008* (2013.01)

(58) Field of Classification Search
CPC .................. A61B 18/1442; A61B 18/1445
See application file for complete search history.

(56) References Cited

U.S. PATENT DOCUMENTS

| | | |
|---|---|---|
| 4,492,231 A | 1/1985 | Auth |
| 5,417,686 A | 5/1995 | Peterson et al. |
| 5,647,871 A | 7/1997 | Levine et al. |

(Continued)

FOREIGN PATENT DOCUMENTS

| | | |
|---|---|---|
| EP | 0582483 A2 | 2/1994 |
| JP | 2004-502488 | 1/2004 |

(Continued)

OTHER PUBLICATIONS

International Search Report dated Jul. 3, 2015 for Application No. PCT/US2015/023283.

(Continued)

*Primary Examiner* — Eric D. Bertram
(74) *Attorney, Agent, or Firm* — The Dobrusin Law Firm, P.C.

(57) ABSTRACT

An electrosurgical device comprising: forceps including: (i) a first working arm; (ii) a second working arm; (iii) a blade electrode; wherein the electrosurgical device is capable of being switched between a first electrical configuration so that the electrosurgical device delivers a first therapy current through the first working arm, the second working arm, or both, and a second electrical configuration so that the electrosurgical device delivers a second therapy current through the blade electrode; and wherein the electrosurgical device includes a heat pipe in the first working arm, the second working arm, or both.

17 Claims, 2 Drawing Sheets

(56) References Cited

U.S. PATENT DOCUMENTS

| | | | |
|---|---|---|---|
| 6,074,389 A * | 6/2000 | Levine | A61B 18/1402 606/45 |
| 6,206,876 B1 | 3/2001 | Levine et al. | |
| 6,679,882 B1 * | 1/2004 | Kornerup | A61B 18/1445 606/46 |
| 6,733,501 B2 | 5/2004 | Levine | |
| 6,832,998 B2 | 12/2004 | Goble | |
| 6,860,882 B2 | 3/2005 | Battles et al. | |
| 6,929,645 B2 | 8/2005 | Battles et al. | |
| 6,942,662 B2 | 9/2005 | Goble et al. | |
| 7,211,084 B2 | 5/2007 | Goble et al. | |
| 7,235,073 B2 * | 6/2007 | Levine | A61B 18/1442 606/25 |
| 7,708,735 B2 * | 5/2010 | Chapman | A61B 18/1442 606/51 |
| 8,100,894 B2 | 1/2012 | Mucko et al. | |
| 8,235,982 B2 | 8/2012 | Ward | |
| 2003/0130658 A1 * | 7/2003 | Goble | A61B 18/14 606/48 |
| 2006/0264929 A1 | 11/2006 | Goble et al. | |
| 2011/0130757 A1 * | 6/2011 | Horlle | A61B 18/1445 606/48 |
| 2011/0270265 A1 | 11/2011 | Fleming | |
| 2011/0306967 A1 | 12/2011 | Payne et al. | |
| 2011/0306968 A1 * | 12/2011 | Beckman | A61B 18/1445 606/41 |
| 2014/0276795 A1 | 9/2014 | Batchelor et al. | |
| 2014/0276799 A1 | 9/2014 | Batchelor et al. | |

FOREIGN PATENT DOCUMENTS

| | | |
|---|---|---|
| JP | 2005-525861 | 9/2005 |
| JP | 2010-517598 | 5/2010 |
| JP | 2014-008406 | 1/2014 |
| WO | 1999/066850 | 12/1999 |

OTHER PUBLICATIONS

Office Action from the Japanese Patent Office for Application JP 2016-560011, dated Sep. 19, 2017.

* cited by examiner

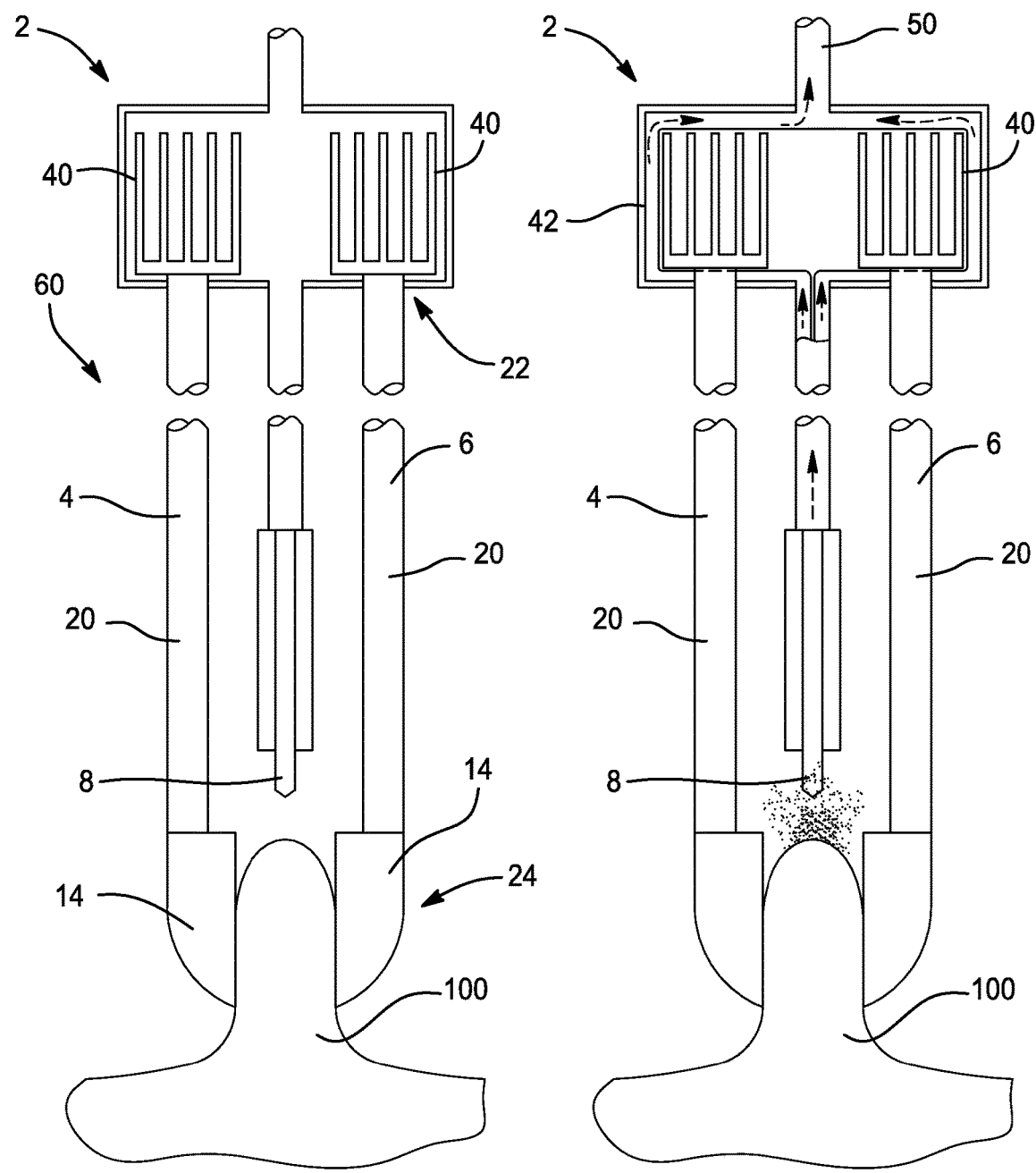

HEAT PIPE COOLING ARRANGEMENT FOR ELECTROSURGICAL DEVICES

FIELD

The present teachings generally relate to an electrosurgical device that includes heat pipes to cool one or more working arms, one or more electrodes, or both; a heat sink to cool the one or more working arms and/or electrodes; a fluid evacuation conduit for removing smoke from a predetermined region; or a combination thereof.

BACKGROUND

Typically, electrosurgical devices have one or more electrodes that are heated when power passes through the electrodes to perform a surgical procedure. These electrodes after performing the surgical procedure may become hotter and hotter and heat may be dissipated from the electrosurgical device through convection. As these electrodes heat up the tendency of tissue to stick to the electrodes and/or working arms may increase. This sticking of tissue may increase the amount of time to perform a surgical procedure, increase bleeding, damage tissue or a combination thereof. Some attempts have been made to circulate a cooling fluid through the electrosurgical device to cool the electrosurgical device during a procedure and/or between uses. The addition of a cooling fluid may require one or more fluid lines that run to and/or from the electrosurgical device, which may restrict movement of the surgeon, add to the weight of the electrosurgical device, add to the complexity of the device, or a combination thereof. Further, a constant flow of fluid may restrict the ability of the user in controlling the temperature of the electrosurgical device and/or components that are desired to remain heated may be cooled and this cooling may affect performance of these components. Some attempts to cool an electrosurgical device may be found in U.S. Pat. Nos. 4,492,231; 5,417,686; 5,647,871; 6,733,501; 6,860,882; and 8,100,694 all of which are incorporated by reference herein for all purposes.

The electrosurgical device when heated may be used to cut tissue, cauterize tissue, coagulate, or a combination thereof. Cutting, cauterization, and coagulation creates smoke that may be inhaled by the user and the smoke may have adverse effects for the user. Recently attempts have been made to increase ventilation in operating rooms to dissipate the smoke as it is created, however, the user may still inhale some surgical smoke. Some attempts have been made to evacuate smoke directly from the electrosurgical device, some examples of which are found in U.S. Pat. No. 8,235,982; U.S. Patent Application Publication No. 2011/0270265; and European Patent Application No. EP0582483 all of which are incorporated by reference herein for all purposes.

It would be attractive to have an electrosurgical device where temperature of the electrosurgical device is controlled so that tissue does not stick to the electrosurgical device. What is needed is an electrosurgical device that evacuates smoke while the smoke is created. What is needed is an electrosurgical device that produces multiple different therapy currents and controls the temperature of the various components depending on the therapy current being used. What is needed is an electrosurgical device that includes a self-contained cooling system that is in communication with a heat sink.

SUMMARY

The present teachings meet one or more of the present needs by providing: an electrosurgical device comprising: forceps including: (i) a first working arm; (ii) a second working arm; (iii) a blade electrode; wherein the electrosurgical device is capable of being switched between a first electrical configuration so that the electrosurgical device delivers a first therapy current through the first working arm, the second working arm, or both, and a second electrical configuration so that the electrosurgical device delivers a second therapy current through the blade electrode; and wherein the electrosurgical device includes a heat pipe in the first working arm, the second working arm, or both.

Another possible embodiment of the present teachings comprises: an electrosurgical device comprising: one or more arms having a proximal end and a distal end; one or more electrodes at the distal end of the one or more arms; one or more fluid evacuation conduits located proximate to the one or more arms so that during use of the electrosurgical device the one or more fluid evacuation conduits move a fluid away from the electrosurgical device; and one or more thermally conductive members connected to the one or more arms, the one or more electrodes, or both; wherein the electrical surgical device includes one or more heat exchange surfaces that deliver heat from the thermally conductive members to the fluid evacuation conduit so that heat generated by the one or more electrodes is removed by the fluid evacuation conduit.

The present teachings provide an electrosurgical device where temperature of the electrosurgical device is controlled so that tissue does not stick to the electrosurgical device. The present teachings provide an electrosurgical device that evacuates smoke while the smoke is created. The present teachings provide an electrosurgical device that produces multiple different therapy currents and controls the temperature of the various components depending on the therapy current being used. The present teachings provide an electrosurgical device that includes a self-contained cooling system that is in communication with a heat sink.

BRIEF DESCRIPTION OF THE DRAWINGS

FIG. 3 illustrates a view of heat sinks connected to heat pipes; and

FIG. 4 illustrates a view of a fluid evacuation conduit extending around heat sinks connected to heat pipes.

DETAILED DESCRIPTION

Figure 1:
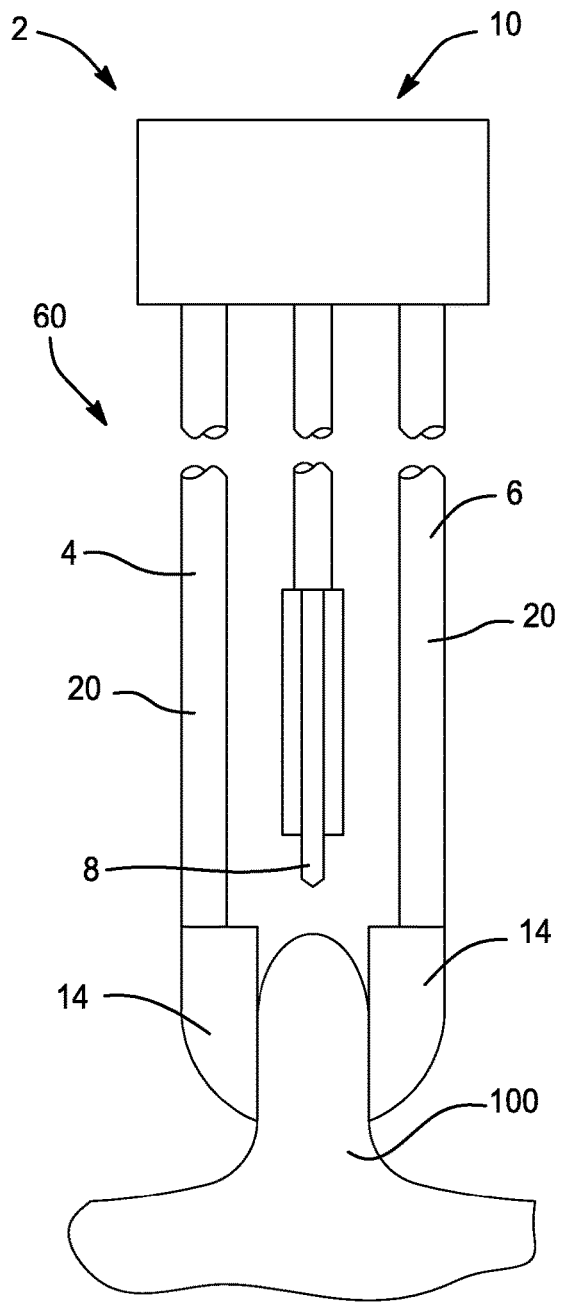
FIG. 1 illustrates an electrosurgical device including heat pipes gripping tissue.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to an electrosurgical system that includes an electrosurgical device. Preferably, the present teachings relate to an electrosurgical device and associated componentry that form an electrosurgical system. The electrosurgical system may include one or more of the devices taught herein. Preferably, the electrical surgical system includes at least one electrosurgical device. More preferably, the electrosurgical system includes an electrosurgical device electrically connected to a generator. The electrosurgical system may include one or more handpieces as taught herein, one or more ground pads, one or more generators, one or more electrosurgical devices, one or more adjacent handpiece components, or a combination thereof and the teachings herein of each device which are incorporated into the electrosurgical system. The electrosurgical device may function to be used by a surgeon to perform a surgical procedure. The electrosurgical device may function to be switched between two or more configurations, two or more states, or both. For example, the electrosurgical device may be switched between a first electrical configuration (e.g., a monopolar configuration), a second electrical configuration (e.g., a bipolar configuration), or a combination of both. The electrosurgical device may be switched between two or more configurations with one hand so that a user may switch between the configurations without the need for a second hand, without disrupting the procedure, or both. The electrosurgical device may be any device and/or configuration that may be used ambidextrously, ambidextrously switched between configurations, or both. The electrosurgical device may be used to cut, perform hemostasis, coagulate, desiccate, fulgurate, electrocautize, or a combination thereof. The electrosurgical device may be any device that includes bipolar capabilities, monopolar capabilities, non-electrosurgical capabilities, or a combination thereof. The electrosurgical device may be used in open surgery. In addition to its electrosurgical capabilities the electrosurgical device may be used for non-electrosurgical purposes. For example, the electrosurgical device may be used as forceps, tweezers, or both that may be used to grip an object, an organ, a vein, skin, tissue, the like, or a combination thereof. The electrosurgical device may be fully and/or partially disposable, reusable, reposable, or a combination thereof. The electrosurgical device may include a handpiece and a generator. The electrosurgical device may have one or more therapy signals that extend between the handpiece and the generator.

The one or more therapy currents may be formed by the handpiece, formed by the generator, or both. The electrosurgical therapy signals may provide a signal so that one or more therapy currents are produced and the therapy currents may be used for electrosurgery. The electrosurgical therapy signals may be a first electrosurgical therapy current, a second electrosurgical therapy current, or both. The first electrosurgical therapy current may be a monopolar therapy current and the second electrosurgical therapy current may be a bipolar therapy current. The electrosurgical therapy signal may be conducted when an activation circuit of the electrosurgical device is in a first switch state, a second switch state, a third switch state, the handpiece is in a first position, a second position, a third position, or a combination of switch states and handpiece is in one of a plurality of positions (e.g., a first position, a second position, or a combination of both). For example, the handpiece in a first position (e.g., a bipolar configuration) may produce a coagulation therapy current when the activation circuit is in a second switch state and a cut therapy current when the activation circuit is in a third switch state. The handpiece in a second position may be a monopolar configuration. Preferably, a therapy signal is not generated, does not exit the handpiece, or both when the activation circuit is in the first switch state. The electrosurgical therapy signal may be a monopolar therapy signal, a bipolar therapy signal, or both. The monopolar therapy signal may be any signal that has a voltage differential between a return port and an active port in the generator. The monopolar therapy signal may be any signal that when applied by the electrosurgical device extends: from one pole of an electrosurgical device to another pole located at a remote location, off of the electrosurgical device (e.g., from the handpiece to a location separate from the handpiece), off of the handpiece, or a combination thereof. The bipolar therapy signal may be any signal that has a voltage differential between two leads that are connected to the electrosurgical device, that are located in the generator, or both. The bipolar therapy signal may be any signal that when applied by the electrosurgical device extends from one component of a handpiece to another component of the handpiece (e.g., between two working arms, from a movable member to one or both working arms, or both). An electrosurgical therapy signal, when the activation circuit is in the second state, may exit the handpiece so that a therapy current extends from a moveable member, between the first working arm and the second working arm, between the moveable member (e.g., a blade electrode or a ground pad) and one or both of the working arms, between a blade electrode and a ground pad, or a combination thereof. The therapy signal may be generated and conducted from the handpiece to the generator or vice versa.

The generator may be any device that supplies: power, a therapy current, control signals, an electrosurgical therapy signal, electrically reconfigures itself in response to a signal from the user and/or mechanical reconfiguration by the user, physically reconfigures in response to adjustments by the user, or a combination thereof. The generator may be any device that may be electrically connected to a handpiece to provide and/or receive electrosurgical therapy signals, power, therapy current, or a combination thereof. The generator may be capable of producing only a single therapy current. The generator may be capable of producing two therapy currents. The generator may be capable of producing a plurality of therapy signals. The generator may include two or more power connections or three or more power connections. The power connections may be any port in the generator that one or more power connectors of the handpiece may be plugged into so that power, control signals, therapy currents, or a combination thereof are supplied to the electrosurgical device. The generator may include one or more switches that may be switched between one or more of the power connections so that power, signals, or both may be selectively applied to the electrosurgical device based upon a desired configuration of the electrosurgical device. The generator may include a central processing unit (CPU). The CPU may electrically reconfigure the electrosurgical device without the need for physical reconfiguration. The CPU may be any device that provides power, signals, electrical reconfiguration, a switch between two or more therapy currents, a switch between two or more configurations, a switch between two or more therapy signals, or a combination thereof to the electrosurgical device so that the electrosurgical device may be used to perform a desired function as is discussed herein. The CPU may be used to switch the electrosurgical device between first electrosurgical configuration, a second electrosurgical configuration, a third electrosurgical configuration, a monopolar configuration, a bipolar configuration, a non-electrosurgical configuration, or a combination thereof.

The non-electrosurgical configuration may be any configuration where power is not supplied to the handpiece, the two or more working arms, or a combination thereof. The non-electrosurgical configuration may be used when the electrosurgical device is being used as forceps, tweezers, a clamp, Kelley hemostat forceps, scalpel, or a combination thereof. In the non-electrosurgical configuration the working arms may be mobile. In the non-electrosurgical configuration the working arms may be immobilized. In the non-electrosurgical configuration the therapy current may not pass through the handpiece, the working arms, the electrosurgical device, or a combination thereof. The handpiece may include two working arms, a blade electrode, a ground pad, or a combination thereof. Preferably, the handpiece includes two integrally connected working arms and a blade electrode and an indirectly connected ground pad.

The device when in a monopolar configuration may supply power between a handpiece component (e.g., a blade electrode) and a return electrode that may be located at another location outside of the hand held portion of the electrosurgical device, through a handpiece component and an adjacent handpiece component, or both. The monopolar configuration may function to apply monopolar power. The monopolar configuration may be used to cut tissue, coagulate blood and/or fluids, electrical cutting, hemostasis, apply power to a large area, or a combination thereof. The monopolar configuration may be used to heat a specific area, heat an object between both electrodes, in contact with both electrodes, or a combination thereof. The electrosurgical device in the monopolar configuration may include a movable blade electrode.

The blade electrode may function to apply current so that current passes between the blade electrode and a distal electrode (e.g., a ground pad). The blade electrode may function to cut tissue and/or an anatomical feature. The blade electrode may extend beyond the working arms, be immobilized between the working arms, pass current to a remote electrode, or a combination thereof. The blade electrode may retain heat during use, not be cooled, be free of a heat pipe, or a combination thereof. The blade electrode may be made of a material that retains heat, has a low thermal conductivity, or both. The blade electrode may be made of a material that conducts electricity, coated with a material that conducts electricity, or both. The blade electrode may include iron, nickel, tungsten, steel, stainless steel, surgical steel, copper, titanium nitride, or a combination thereof. The blade electrode may be made of tungsten. Preferably, the blade electrode is made of steel. The blade electrode may include a coating that prevents the blade electrode from rapidly dissipating heat, from passing heat to the working arms, or both. The blade electrode may be retracted so that when the device is in a forceps configuration, a bipolar configuration, or both the blade electrode does not interfere with the working arms.

The device when in a bipolar configuration may supply power from one portion of the device to a second portion of the device so that the return path for the power is relatively short when compared to the monopolar configuration. The bipolar configuration may be any configuration where the electrosurgical device may be used to apply bipolar power. The device when in the bipolar configuration may supply power between two localized handpiece components such as two working arms. The bipolar configuration may be used to coagulate, for hemostasis, cutting, fulguration, or a combination thereof. When in the bipolar configuration the electrosurgical device may include two opposing working arms. The two opposing working arms may be configured as forceps.

The forceps may function to grip, hold, squeeze, or a combination thereof one or more objects. The forceps may include one or more finger grips (i.e., configured like scissors) that may be used to move the forceps so that the forceps may be used to grip one or more objects. The forceps may be free of finger grips and be actuated by direct pressure being applied to opposing sides of the forceps so that the forceps close and grip an object. The forceps may include at least two working arms, a blade electrode, or a combination of both.

The working arms may be any part of the electrosurgical device that may be used to grip, hold, squeeze, or a combination thereof an object when the object is between the two or more opposing working arms. The working arms may include one or more gripping features that may assist in gripping, holding, squeezing, or a combination thereof an object. The working arms may be movable between two or more positions. Preferably, the working arms are movable between at least a first position and a second position. For example, the working arms may be movable between a bipolar configuration (e.g., first position) and a monopolar configuration (e.g., second position). The working arms in the first position may be off, energized, one working arm may be energized, or a combination thereof. The working arms in the second position may be off, one or both of the working arms may be electrically disconnected, one or both of the working arms may be electrically connected, one working arm may be shorted by the other working arm, or a combination thereof. More preferably, in the second position one or both of the working arms are immobilized so that the working arms cannot be used a forceps. The working arms may be longitudinally static and moveable relative to each other. Preferably, at least one of the working arms is both longitudinally movable (e.g., movable along the length of the handpiece) and laterally movable (e.g., movable towards and away from an opposing working arm). The working arms may be selectively retractable and/or extendable so that one or more tip regions are exposed.

The working arms, the blade electrode, or both ray include a tip region. The tip region may include a portion that is configured to assist in facilitating gripping, holding, squeezing, transferring of a therapy current, or a combination thereof. The tip region may be located at a distal end of the forceps. The tip region may be located at a distal end of the working arms, the blade electrode, or both. The tip region may be configured in one or more electrosurgical configurations (e.g., a monopolar configuration, bipolar configuration, or a combination of both). The tip region may include teeth, serrations, mouse teeth, be free of teeth (i.e., smooth), or a combination thereof. The tip region may be fully and/or partially insulated. Preferably, the tip region includes insulation on the non-contact portions of the working arms and/or blade electrode so that electrosurgical energy is not transferred through incidental contact. The working arms may include an active portion and an inactive portion (i.e., an insulated portion).

The active portion may be any portion of the device that may be used to apply power. The active portion may be the same portion as the contact regions of the forceps and/or blade electrode. Thus, for example, when tissue is grasped between the contact portions of the forceps, power may be supplied to the tissue through this contact portion. The active portion of the working arms preferably is between the two opposing working arms, the active portion during a monopolar configuration is part of a single working arm, or both. The active portions may be substantially surrounded by inactive portions or portions that are insulated. The inactive portion may be any portion that does not supply power, that is insulated, or both. The inactive portion may be any portion that may prevent a transfer of power through incidental contact and thus are insulated so that an incidental transfer of power does not occur. For example, an outside of the working arms may be coated with an insulating material so that if the working arms accidentally contact tissue proximate to the tissue of interest the proximate tissue is not subjected to a transfer of power. The inactive portion and the active portion may be made of different materials, coated with different materials, or both.

The working arms may be made of any material that may be used to grip, hold, squeeze, or a combination thereof and provide monopolar power, bipolar power, a therapy current, a gripping force, or a combination thereof to a desired location. The working arms may be made of one material and the tip region of each working arm may include or be coated with one or more materials that may be insulating, a higher thermal conductivity than the base material, a lower thermal conductivity than the base material, or a combination thereof. Each of the working arms may include a material with a thermal conductivity and the thermal conductivity of the working arms may be the same, one working arm may be higher than the other working arm, or both. The one or more working arms may include one or more materials along the length of the working arm. For example, the working arms may be entirely made of stainless steel. Preferably, each working arm includes two or more materials. For example, the working arms may have a base material of stainless steel and the working arms may be coated with an insulating material such as silicone or polytetrafluoroethylene (PTFE). The working arms may include any material that is safe for use in a surgical procedure, and preferably in an electrosurgical procedure. The working arms may include metals, plastics, a polymer, an elastomer, gold, silver, copper, titanium, aluminum, iron based metals, stainless steel, silicone, polytetrafluoroethylene (PTFE), insulating polymers, rubber, or a combination thereof. Preferably, each working arm is substantially coated with an insulating material except for a contact region between the two working arms where the working arms contact each other. The working arms may be coated in regions where the user contacts the working arms. The working arms may include an insulating material where the working arms contact a blade electrode so that heat from the blade electrode is not transferred to the working arms. The material of the working arms, a coating on the working, arms, a housing of the working arms, or a combination thereof may prevent a dissipation of heat from the working arms. The working arms may apply a cut therapy current, a coagulation therapy current, or both. The working arms due to continued use during an electrosurgical procedure may increase the temperature of the working arms. The working arms may be insulated from the blade so that thermal energy or electrical energy is prevented from being transferred to the working arms (e.g., the blade, working arms, or both may include an insulating coating). The working arms may each include one or more heat pipes that may assist in facilitating dissipation of heat, may dissipate heat, or both.

The one or more heat pipe may function to transfer heat from a region of a greater concentration of heat to a region with a lower concentration of heat. The heat pipe may function to carry heat from a first location to a second location where the heat is dissipated. The heat pipe may carry heat from a distal end of the electrosurgical device, the working arms, or both to a proximal end (i.e., an end of the device and/or arms closest to the user), a central portion (e.g., a portion of the working arms between the distal end and the proximal end), or a combination of both of the electrosurgical device, the working arms, or both. The one or more heat pipes may be integrally connected to the electrodes of the working arms, the blade electrode, or both. Preferably, the one or more heat pipes are not connected to or in contact with the blade electrode. The one or more heat pipes may be located parallel to the working arms and/or a portion of the working arms that become heated so that heat is transferred from the working arms to the heat pipe. The heat pipes may surround a portion of the working arms that become heated during use. The heat pipes may have an increased surface area at a point of contact with the working arms, an electrode of the working arms, a heated portion of the working arms, or a combination thereof. The heat pipes may be part of the working arm electrodes and a closing end of the heat pipes may contact tissue, may be the electrosurgical electrode, or both. For example, a closed end of the heat pipe may be exposed and may contact tissue to provide a therapy current to a feature of interest. The one or more heat pipes may be sealed, self-contained, a vacuum, or a combination thereof. The one or more heat pipes may be sealed, self-contained, a vacuum, or a combination thereof so that additional fluid is not needed to perform a cooling function. The one or more heat pipes may include a fluid to absorb heat, remove heat, dissipate heat, or a combination thereof. The one or more heat pipes may be filled with water, alcohol, sodium, ammonia, ethanol, methanol, or a combination thereof. The fluid may undergo one or more phase changes and preferably two or more phase changes (e.g., evaporation, condensation, or both) that assist in removing heat from the working arms, the electrosurgical device, or both. The one or more heat pipes may function so that the fluid sealed within the heat pipe when heated evaporates from the distal end and moves to the proximal end where the fluid condenses and releases the heat. The condensate then moves from the proximal end back to the distal end and the cycle repeats.

The heat pipe may be sufficiently long and/or have a sufficiently large cross-sectional thickness (e.g., diameter) so that fluid travels from the distal end of the heat pipe to the proximal end of the heat pipe so that the fluid is cooled. The heat pipe may be sufficiently long and/or have a sufficient cross-sectional thickness so that evaporated fluid travels from the hot end of the heat pipe (e.g., distal end) to the cool end of the heat pipe (e.g., proximal end) where the fluid condenses. The heat pipe may be sufficiently long and/or have a sufficient cross-sectional thickness so that the proximal end remains sufficiently cool so that the evaporated fluid condenses. The length and/or cross-sectional thickness may be sufficiently large so that the heat pipe continues to cool over an extended duration of use (e.g., about 10 minutes or more, about 20 minutes or more, about 30 minutes or more, or even about 1 hour or more of substantially continuous use). The fluid when condensed may travel from the cool end to the hot end via capillary action, centrifugal force, gravity, or a combination thereof. The heat pipe may include a sufficient amount of fluid so that the heat pipe substantially maintains a constant temperature of the working arms, the electrosurgical device, or both for the duration of use. The heat pipe may include a sufficient amount of fluid so that the temperature of the heat pipe raises by a temperature of about 40° C. or less, about 30° C. or less, about 20° C. or less, or about 10° C. or less over the duration of use, over an extended duration of use, or both. Each of the one or more heat pipes may be connected to one or more heat sinks.

The one or more heat sinks may be connected to the one or more heat pipes. Each heat pipe may be connected to a heat sink, have an integral heat sink, or both. The heat pipes may extend through the heat sinks and the heat sinks may remove heat from the heat pipe through thermal contact. The heat pipe may transfer heat to the heat sink via a heat transfer medium (e.g., a thermal paste) so that heat is transferred from the heat pipe to the heat sink. The heat sink and the heat pipes may be made of the same material. The heat sink may be an extended portion of the heat pipe that acts to dissipate heat. For example a coil or other extended shape may extend from the an end of the heat pipe and may allow for heat transfer. The heat sink may be located on the cold end of the heat pipe, on the proximal end of the heat pipe, the proximal end of the working arms, the proximal end of the electrosurgical device, or a combination thereof. The heat sink may increase the surface area of each of the one or more heat pipes. The heat sink may include one or more heat exchange surfaces that dissipate heat from the fluid. The one or more heat exchange surface may increase the surface area of the heat exchanger relative to the heat pipe so that heat is dissipated. The surface area of the heat exchange surface may be about two times or more, about three times or more, or even about four times or more than the surface area of the heat pipe. The one or more heat exchange surfaces may be and/or include fins, baffles, an increase in surface area, tubes, plates, ribs, or a combination thereof. The heat sink may be located on the hand piece, on a proximal end of the handpiece, on a distal end of the hand piece, on the working arms, on a proximal end of the working arms, on a central portion of the handpiece, or a combination thereof. The heat sink may be an integral part of the working arms so, that movement of the working arms moves the heat sink or vice versa. The heat sink, heat pipe, or both may be partially and or entirely shielded from contact by the user so that heat from the heat pipe, the heat sink, or both does not directly contact the user. The heat sink may be made of the same material as the heat pipe. The heat sink may be made of a material with high conductivity, higher conductivity than the heat pipe, or both. The heat sink may use natural convection, forced convection, or both to dissipate heat. Movement of the electrosurgical device during use may force air over the heat sink, the heat exchange surface, or both and dissipate heat. The electrosurgical device may include one or more fluid evacuation conduits that may move air across the heat sink, the heat pipe, or both.

The one or more fluid evacuation conduits may function to remove smoke and/or air during an electrosurgical procedure. The fluid evacuation conduits may function to draw air from a point of interest so that at least localized air movement is created. The fluid evacuation conduit may function to circulate air around an electrosurgical device so that the electrosurgical device is cooled. The fluid evacuation conduits may be an integral part of the working arms, the blade electrode, or both. The fluid evacuation conduits may be in communication with the blade electrode. For example, the fluid evacuation conduits may be connected to the blade electrode, extend proximate to the blade electrode and the suction flow across the blade electrode, or both. The fluid evacuation conduit may be connected to one or both working arms, a blade electrode, or both so that air is removed from a region proximate to the distal end of the electrosurgical device during performance of a surgical procedure. The one or more fluid evacuation conduits may move a sufficient amount of air so that a majority (i.e., 50 percent or more, 60 percent or more, 75 percent or more, or even 90 percent or more) of the smoke is removed from the tips of the electrosurgical device as the smoke is created. Each of the one or more fluid evacuation conduits may move about 0.03 m$^3$/min or more about 0.15 m$^3$/min or more, about 0.3 m$^3$/min or more, or even about 0.75 m$^3$/min or more. The fluid evacuation conduits may be on all time the electrosurgical device is connected to a power source, a vacuum source, or both. The fluid evacuation conduits may turn on only when a therapy current is being applied. The one or more fluid evacuation conduits may be statically located on the electrosurgical device. The fluid evacuation conduits may be movable on the electrosurgical device so that the fluid evacuation conduit may be moved to a location of smoke creation. The fluid evacuation conduit may be a series of holes in a tip region of the working arms, the blade electrode, or both. The fluid evacuation conduit may be a series of holes along a length of the working arms, the blade electrode or both. Preferably, the fluid evacuation conduit is connected to the blade electrode and is movable with the blade elected when the blade electrode moves from a first position to a second position (e.g., is extended and retracted).

FIG. 1 illustrates a side view of forceps 2. The forceps 2 include a first working arm 4 and a second working arm 6 that are connected by a handpiece 10. A blade electrode 8 extends from the handpiece 10 between the first working arm 4 and the second working 6. The first working arm 4 and second working arm 6 are movable relative to each other to grip tissue 100 when the in the coagulation mode 60 and with the blade electrode 8 being retracted. Both the first working arm 4 and the second working arm 8 include a heat pipe 20 that removes heat from the tips 14 of the first working arm 4 and the second working arm 6 so that the tips 14 of the first working arm 4 and the second working arm 6 are cooled.

Figure 2:
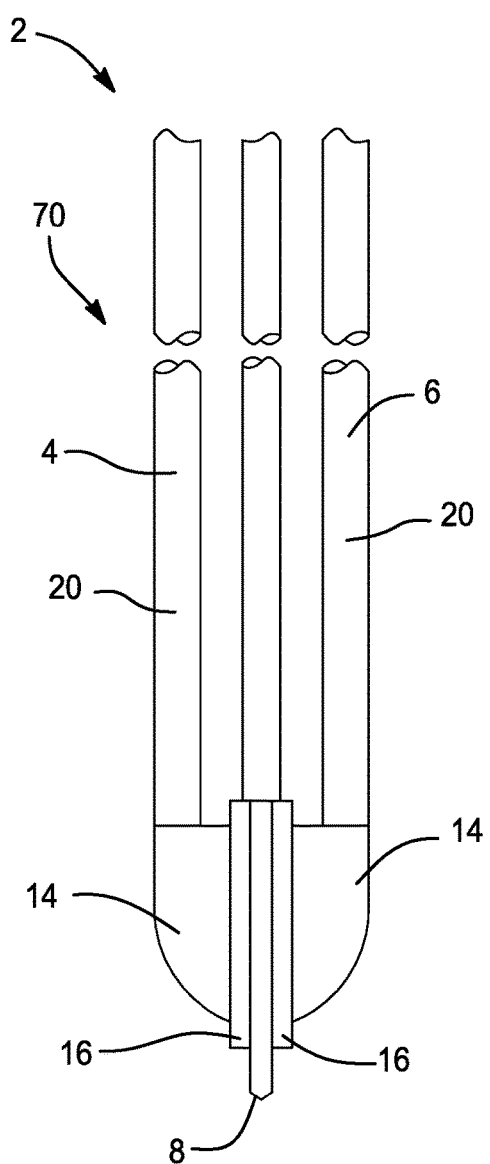
FIG. 2 illustrates the electrosurgical device including a heat pipes and a blade electrode.

FIG. 2 illustrates a side view of forceps 2 in a cut mode 70. The blade electrode 8 is extended between the first working arm 4 and the second working arm 6 so that a portion of the blade electrode 8 extends beyond the tips 14 of the first working arm 4 and the second working arm 6 for performing a cutting function. The forceps 2 include a first working arm 4 and a second working arm 6 that each include a heat pipe 20 for cooling the first working arm 4 and the second working arm 6, and the blade electrode 8 includes insulation 16 that shields the blade electrode 8 from the cooling effects of the heat pipes 20 in the first working arm 4 and the second working arm 6.

FIG. 3 illustrates forceps 2 in the coagulation mode 60 with the blade electrode 8 retracted between the first working arm 4 and the second working arm 6. The first working arm 4 and second working arm 6 are gripping tissue 100 so that a therapy current can be passed between the first working arm 4 and second working arm 6 and through the tissue 100. Both the first working arm 4 and second working arm 6 include a heat pipe 20 having a distal end 24 located near the tips 14 and a proximal end 22 located near and in communication with heat sinks 40 that dissipate heat from the heat pipes 20 cooling the first working arm 4 and the second working arm 6.

FIG. 4 illustrates forceps 2 that include a fluid evacuation conduit 50 that is connected to the blade electrode 8 and extends between the first working arm 4 and the second working arm 6 so that as a therapy current is passed between the first working arm 4 and the second working arm 6 the therapy current passes through tissue 100. As the therapy current is passed through the tissue 100 smoke may be created and any smoke that is created is pulled into the fluid evacuation conduit 50 so that a majority of the smoke is evacuated before the smoke spreads away from the forceps 2. As the therapy current is passed between the first working arm 4 and the second working arm 6, the heat pipes 20 cool the first working arm 4 and the second working arm 6. The heat pipes 20 are in communication with heat sinks 40 that include a heat exchange surface 42 for dissipating heat from the heat pipes 20 to the fluid evacuation conduit 50 so that as air, fluid, smoke, or a combination thereof is moved through the fluid evacuation conduit 50 the heat sinks 40 are cooled.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. An electrosurgical device comprising:
   a forceps including:
   i) a handpiece;
   ii) a first working arm including an electrode;
   iii) a second working arm including an electrode;
   iv) a blade electrode;
   v) one or more heat pipes in the first working arm, the second working arm, or both, wherein the one or more heat pipes are sealed with a closed proximal end and a closed distal end, and wherein the one or more heat pipes include a fluid sealed within the one or more heat pipes;
   vi) one or more heat sinks located on the handpiece, and wherein the one or more heat sinks are connected to the one or more heat pipes,
   vii) one or more fluid evacuation conduits having one or more openings and configured to remove smoke, air, or both from a region proximate to the first working arm, the second working arm, or both, and to move the air across the one or more heat sinks so that heat is dissipated from the one or more heat sinks through forced convection;
   wherein the electrosurgical device is capable of being switched between a first electrical configuration so that the electrosurgical device delivers a first therapy current through the first working arm, the second working arm, or both, and a second electrical configuration so that the electrosurgical device delivers a second therapy current through the blade electrode;
   wherein the closed distal end of the one or more heat pipes is in contact with the electrode of the first working arm, the electrode of the second working arm, or both; and
   wherein the first working arm is moveable toward and away from the second working arm, the second working arm is moveable toward and away from the first working arm, or both.

2. The electrosurgical device of claim 1, wherein the first working arm and the second working arm each include one of the one or more heat pipes.

3. The electrosurgical device of claim 1, wherein the closed proximal end extends into or near a central portion of the forceps.

4. The electrosurgical device of claim 3, wherein the central portion includes the handpiece that a user grips during use, connects the first working arm and the second working arm, or both.

5. The electrosurgical device of claim 3, the fluid in the one or more heat pipes transfers heat from the closed distal end of the one or more heat pipes to the closed proximal end so that a tip of the first working arm, the second working arm, or both is cooled during use.

6. The electrosurgical device of claim 1, wherein the one or more fluid evacuation conduits is connected to the blade electrode.

7. The electrosurgical device of claim 1, wherein the first working arm, the second working arm, or both include one of the one or more heat sinks.

8. The electrosurgical device of claim 7, wherein the one or more heat sinks in the first working arm, the second working arm, or both are connected to the closed proximal end of the one or more heat pipes in the first working arm, the second working arm or both.

9. The electrosurgical device of claim 7, wherein the one or more heat sinks includes a heat exchange surface that is in contact with the one or more heat sinks so that fluid moving through the one or more fluid evacuation conduits removes the heat from the one or more heat sinks.

10. The electrosurgical device of claim 1, wherein the blade electrode includes insulation so that when the blade electrode is extended between the first working arm and the second working arm the blade electrode is insulated from cooling effects of the one or more heat pipes.

11. The electrosurgical device of claim 1, wherein the one or more fluid evacuation conduits are connected to a vacuum source and are configured to suction the smoke, the air, or both away from the electrosurgical device.

12. The electrosurgical device of claim 1, wherein the one or more fluid evacuation conduits include a series of holes in the blade electrode.

13. An electrosurgical device comprising
a) a handpiece;
b) one or more arms having a proximal end and a distal end;
c) one or more electrodes at the distal end of the one or more arms;
d) a blade electrode;
e) one or more fluid evacuation conduits having one or more openings, connected to the blade electrode, and located proximate to the one or more arms so that during use of the electrosurgical device the one or more fluid evacuation conduits move smoke, air, or both away from the electrosurgical device;
f) one or more heat pipes connected to the one or more arms, the one or more electrodes, or both, wherein the one or more heat pipes are vacuum sealed with a closed proximal end and a closed distal end, and wherein the one or more heat pipes include a fluid sealed within the one or more heat pipes;
g) one or more heat sinks which includes one or more heat exchange surfaces, and the one or more heat sinks are located in the handpiece and between the one or more heat pipes and the one or more fluid evacuation conduits; and
wherein the one or more fluid evacuation conduits are configured to move the air across the one or more heat sinks during use so that heat is dissipated away from the one or more heat sinks through forced convection.

14. The electrosurgical device of claim 13, wherein the electrosurgical device is forceps and the one or more arms are a first working arm and a second working arm;
the blade electrode is movable relative to and extends between the first working arm and the second working arm; and
wherein the electrosurgical device is capable of being switched between a first electrical configuration where the electrosurgical device delivers a first therapy current through the first working arm, the second working arm, or both, and a second electrical configuration where the electrosurgical device delivers a second therapy current through the blade electrode.

15. The electrosurgical device of claim 13, wherein the one or more arms are in communication with the one or more heat sinks.

16. The electrosurgical device of claim 13, wherein the one or more fluid evacuation conduits are connected to a vacuum source and configured to suction the smoke, the air, or both away from the electrosurgical device.

17. The electrosurgical device of claim 13, wherein the one or more fluid evacuation conduits are in fluid communication with the handpiece, the one or more heat sinks, or both.

* * * * *